(12) United States Patent
Renger et al.

(10) Patent No.: US 8,915,939 B2
(45) Date of Patent: Dec. 23, 2014

(54) TUBULAR MEDICAL INSTRUMENT

(75) Inventors: Uwe Renger, Hilzingen (DE); Martin Blocher, Tuttlingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1727 days.

(21) Appl. No.: 11/840,301

(22) Filed: Aug. 17, 2007

(65) Prior Publication Data
US 2008/0046001 A1 Feb. 21, 2008

(30) Foreign Application Priority Data
Aug. 17, 2006 (DE) .......................... 10 2006 038 516

(51) Int. Cl.
*A61B 17/00* (2006.01)
*A61B 17/29* (2006.01)

(52) U.S. Cl.
CPC ......... *A61B 17/29* (2013.01); *A61B 2017/2939* (2013.01); *A61B 2017/2902* (2013.01); *A61B 2017/0046* (2013.01); *A61B 2017/292* (2013.01); *A61B 17/00234* (2013.01); *A61B 2017/2901* (2013.01)
USPC ............. 606/205; 606/206; 606/207; 81/418; 81/419; 81/424.5; 81/426; 81/426.5

(58) Field of Classification Search
USPC ......... 606/205–207; 81/418, 419, 424.5, 426, 81/426.5
See application file for complete search history.

(56) References Cited

U.S. PATENT DOCUMENTS

| 5,478,347 A | 12/1995 | Aranyi |
| 5,603,723 A | 2/1997 | Aranyi et al. |
| 5,893,875 A * | 4/1999 | O'Connor et al. ............ 606/205 |

FOREIGN PATENT DOCUMENTS

| DE | 9317535 U1 | 1/1994 |
| DE | 202007003114 U1 | 6/2007 |

OTHER PUBLICATIONS

European Search Report, Application No. 07015338.2, Nov. 19, 2008, 11 pages.

* cited by examiner

*Primary Examiner* — Victor Nguyen
*Assistant Examiner* — Kevin Everage
(74) *Attorney, Agent, or Firm* — St. Onge Steward Johnston & Reens LLC

(57) ABSTRACT

The invention relates to a tubular medical instrument having a hollow shaft, a handle positioned on the proximal end of the shaft, and at least one tool actuation element that is positioned in the hollow shaft and has on its distal end a tool, wherein the tool actuation element can be coupled with at least one actuation mechanism of the handle to actuate the tool and wherein the tool actuation element and the hollow shaft can be detachably connected to one another by a coupling mechanism. To create a coupling mechanism that is essentially free of any play and is simple to operate, it is proposed with the invention that the stopping of the coupling mechanism between the tool actuation element and the hollow shaft should be dependent on the position of the tool.

24 Claims, 6 Drawing Sheets

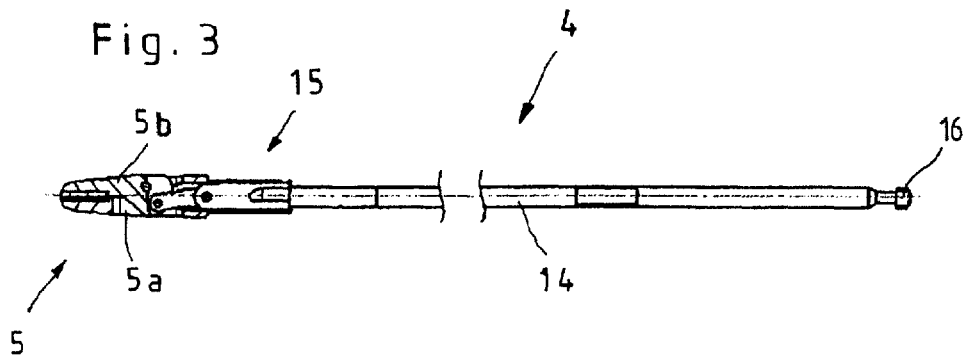
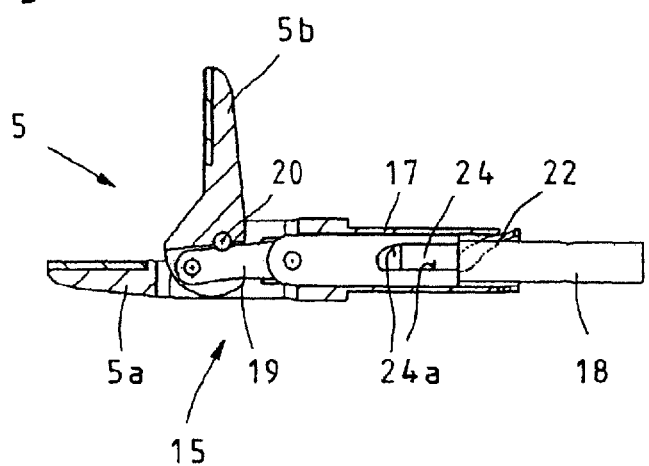
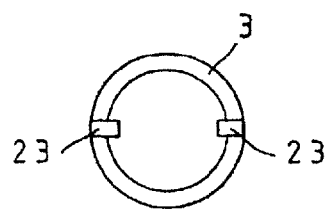

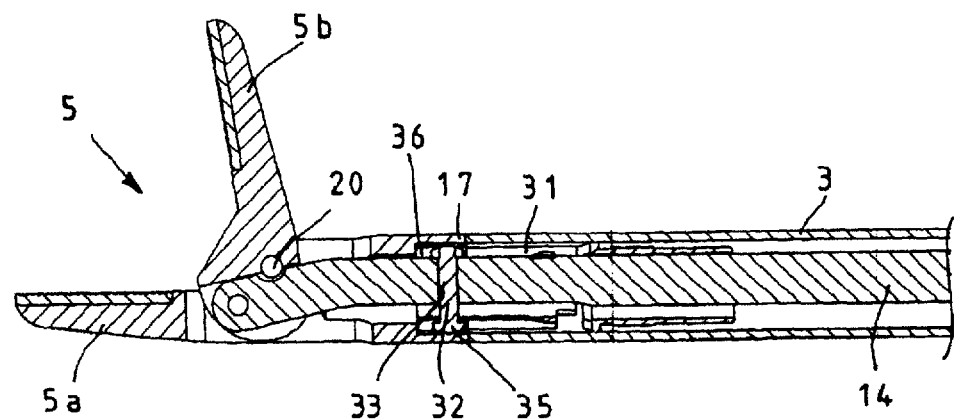
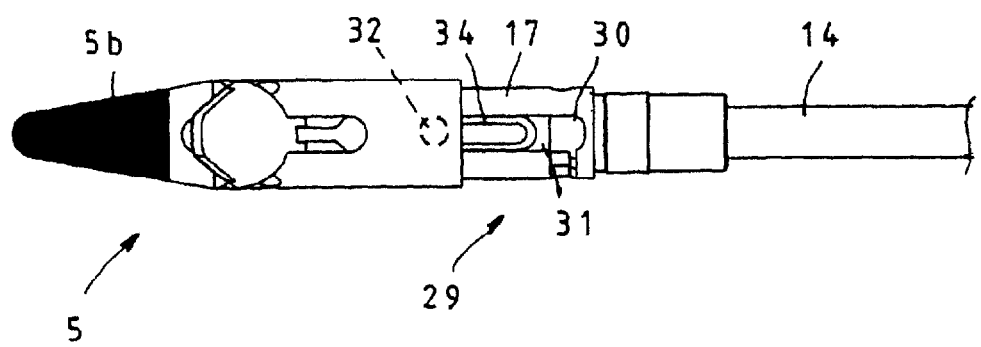

TUBULAR MEDICAL INSTRUMENT

CROSS-REFERENCE TO RELATED APPLICATIONS

The present application claims priority of German patent application No. 10 2006 038 516.0 filed on Aug. 17, 2006, the content of which is incorporated herein by reference.

FIELD OF THE INVENTION

The invention relates to a tubular medical instrument having a hollow shaft, a handle positioned on the proximal end of the shaft, and at least one tool actuation element that is positioned in the hollow shaft and has on its distal end a tool, and wherein the tool actuation element can be coupled with at least one actuation mechanism of the handle to actuate the tool and wherein the tool actuation element and the hollow shaft can be detachably connected to one another by a coupling mechanism.

BACKGROUND OF THE INVENTION

Tubular medical instruments of this type are used, for instance, in the configuration as needle holder, in endoscopic surgery. Because of increasingly stringent hygienic demands, it is more and more often required that tubular instruments, particularly those comprising hollow spaces such as hollow shafts, should be configured so that they can be at least partially dismantled so that they can be submitted to thorough cleansing and sterilization, preferably by steam.

A generic tubular medical instrument, configured as a medical forceps, is reported in DE 43 07 539 A1. This known tubular instrument can be broken down for cleansing and sterilization into three main groups: the tool actuation element configured as a push-pull rod, the hollow shaft, and the handle. The coupling mechanism for connecting the push-pull rod and the hollow shaft, in this construction, is configured as a bayonet-type connection. The bayonet-type connection has proved itself in practice, but its use in installing the instrument requires a certain amount of practice.

It is consequently the object of the invention to perfect a tubular medical instrument in such a way that the tool actuation element and the hollow shaft can be detachably connected to one another by a coupling mechanism that is essentially without free play and also simple to operate.

SUMMARY OF THE INVENTION

This object is fulfilled by the invention in a manner characterized in that the stopping of the coupling mechanism between the tool actuation element and the hollow shaft is dependent on the position of the tool.

This inventive configuration of the coupling mechanism, which is advantageously configured in such a way that the tool actuation element can be connected with the hollow shaft by means of the coupling mechanism exclusively when the tool is in an installation position that differs from the working positions, ensures that no accidental breaking of the connection between the tool actuation element and the hollow shaft can occur during normal working operation.

According to a preferred embodiment of the invention, it is proposed that the tool actuation element should be capable of being connected with the hollow shaft by the coupling mechanism exclusively in an installation position that differs from the working position of the tool. This configuration ensures that the coupling between the tool actuation element and the hollow shaft cannot occur accidentally during normal operation, because the tool can assume this installation position only when the instrument is at least partly dismantled.

According to a first practical embodiment of the invention, the coupling mechanism is configured in the manner of a bayonet-type connection.

With a second configuration of the invention, it is proposed that the coupling mechanism should be configured as a self-locking peg-and-groove control.

The self-locking configuration of the peg-and-groove control ensures that on completion of the coupling of the two components that are to be connected to one another, said components cannot accidentally be severed from one another again, for instance during the continuing installation of the instrument. As a result, the installation becomes considerably simplified and can also be conducted in a manner that is easy and safe for unpracticed users.

To configure the self-locking coupling, it is proposed with the invention that the peg-and-groove control should consist of at least one control peg configured on one of the components that are to be coupled together, and of at least one guide track configured on the other respective component for insertion of a control peg, and that at least one control peg inserted in a guide track should be blocked with the tool in the working position to prevent removal from the guide track.

According to a practical embodiment of the invention, the at least one control peg is configured on the distal side on the inside of the hollow shaft. A control peg is preferably configured on the inside of the distal end of the hollow shaft, and two guide tracks for insertion of the control peg, situated opposite to one another, are preferably configured on the distal end of the tool actuation element. The use of two guide tracks opposite to one another, even with just one control peg, has the advantage that the two components that are to be coupled together can be coupled to one another in more than just a single position of the components with respect to one another, thus simplifying the installation. It is also possible of course to provide two control pegs and two guide tracks, and the control peg and guide tracks must be positioned, corresponding to one another, on the periphery of the shaft or of the tool actuation element.

The actuation mechanism of the handle, by which the tool actuation element and thus also the tool can be actuated, is advantageously configured, according to the invention, as a gripping member that is positioned to rotate on the handle.

It is proposed with another practical embodiment of the invention that the tool should be configured as a tool consisting of at least two jaw members, such that at least one jaw member of the tool can be rotated with respect to the other jaw member by the tool actuation element.

According to a preferred embodiment of the invention it is proposed that the tool actuation element should be configured as a push-pull rod.

It is further proposed with the invention that this tool actuation element configured as a push-pull rod should consist of a rod base body and a tool assembly that is firmly connected with the rod base body and forms the distal end of the push-pull rod. The two-art configuration of the push-pull rod makes it possible that for the configuration of the widest range of tubular instruments a constantly uniform rod base body, which varies only in terms of length, must be produced. For final production of a concrete tubular instrument it is then necessary only to connect the respective required tool assembly firmly with the rod base body, for instance by soldering.

According to a preferred embodiment of the invention, it is proposed that the tool assembly should consist of a sleeve equipped with a rigid jaw member of the tool and a tool shaft that is mounted so that it can slide within the sleeve and which, on the one hand, is coupled with a rotatable jaw member of the tool and, on the other hand, can be connected firmly with the rod base body, such that the guide track for insertion of a control peg is preferably configured in the sleeve of the tool assembly. This construction, in which the sleeve configured as a single unit with the rigid jaw member is supported on the hollow shaft and the tool shaft mounted so that it can slide within the sleeve is connected firmly with the rod base body of the push-pull rod, makes possible a direct force transmission, without play, of the pushing or pulling forces applied by the handle on the push-pull rod onto the rotatable jaw member of the tool. The guide track is preferably configured in helical shape and, according to the invention, comprises a gradient angle Alpha, which depends on the frictional pairing and should not exceed a predetermined maximum gradient of preferably 45 degrees in order to prevent self-locking of the control peg in the guide track during installation or dismantling.

To ensure that the tool actuation element and the hollow shaft can be coupled with one another and released again, with the tool exclusively in an assembly position that differs from the working positions, it is proposed with the invention that in the area of the proximal end of the tool actuation element that is mounted in the handle and of the hollow shaft, a limiting device is positioned that limits the mobility of the tool actuation element inside the hollow shaft. This limiting device, on the one hand, restricts the path of the axial sliding of the tool actuation element within the hollow shaft, so that this element can be pushed only to the point where the tool can be displaced from the closed working position into the open working position and back, and on the other hand, the limiting device prevents a rotation of the tool actuation element around its longitudinal axis if this element is not configured as a torsion element.

The inventive limiting device consists preferably of at least one contact surface configured on the tool actuation element and of a contact element that is mounted in the hollow shaft and can be brought into active connection with this contact surface.

With a practical embodiment for the configuration of the limiting device, it is proposed that two opposite contact surfaces configured as recesses should be positioned on the tool actuation element and that a contact element should be mounted in a recess in the hollow shaft and, with the tool actuation element and hollow shaft installed, should be in essentially form-locking contact with one of the contact surfaces of the tool actuation element. When the tool actuation element and hollow shaft are installed and connected with the handle, the contact element, interacting in essentially form-locking contact with one of the contact surfaces of the tool actuation element, blocks an axial sliding of the tool actuation element beyond the extent required for converting the tool into the open working position. Thanks to the inventive limiting device, accidental conversion of the tool into the installation position is reliable prevented.

It is further proposed with the invention that the tool shaft and the rotatable jaw member should be connected to one another by at least one articulated lever that is positioned so that it can rotate on both sides, in order to ensure better force transmission to the jaw member.

When the hollow shaft and the tool actuation element are installed and coupled to one another, to secure the control peg that is completely inserted in the guide track, it is proposed with the invention that an open recess for insertion of the control peg should be configured on the proximal side running in the axial direction of the tool shaft in the tool shaft of the tool assembly, in such a way that at least one of the edges of the recess running essentially parallel to one another in the axial direction of the tool shaft, with the tool in the working position, should form a limiting abutment surface for the control peg.

It is finally proposed with the invention that the tool for uncoupling the tool actuation element from the hollow shaft should be able to be converted into the installation position by a light "blow" on the proximal end of the tool actuation element uncoupled from the handle. It is likewise possible to convert the tool into the installation position by hand, for instance by pressing on the proximal end of the tool actuation element that is uncoupled from the handle relative to the hollow shaft. This way of moving the tool actuation element into the installation position ensures that the inventive tubular medical instrument can never be accidentally converted, in assembled working position, into the installation position that separates the hollow shaft and the tool actuation element.

With another embodiment it is proposed with the invention that the tool actuation element configured as a push-pull rod should consist of a rod base body and a tool assembly that makes up the distal end of the push-pull rod and can be firmly connected with the rod base body, in such a way that the tool assembly consists of a sleeve equipped with a rigid jaw member of the tool and a guide assembly that is positioned in the sleeve and coaxially surrounds the distal end of the push-pull rod In the installed condition, to prevent rotation of the push-pull rod and thus of the jaw members as well, which would cause the release of the bayonet-type connection, the push-pull rod according to the invention comprises, in the distal end mounted in the guide set, a locking bolt positioned perpendicular to the longitudinal axis of the push-pull rod, which is mounted so that it can move freely in a bore-hole of the push-pull rod in such a way that the free ends of the locking bolt in the guide set extend through the configured guide tracks and thus block any rotary movement.

It is further proposed with the invention that the free ends of the locking bolt should be configured as bold-head-shaped thickenings in order to prevent the locking rods from slipping out of the guide tracks and of the bore-hole.

Further characteristics and advantages of the invention can be seen from the appended drawing, in which two embodiments of an inventive tubular medical instrument are depicted in merely schematic form, without restricting the invention to these embodiments.

BRIEF DESCRIPTION OF THE DRAWINGS

FIG. 3 shows a partly cut-out schematic side view of the push-pull rod according to FIG. 2, but showing the tool in the closed working position.

FIG. 4 shows an enlarged, partly cut-out side view of a first embodiment of detail IV according to FIG. 1, but showing the tool in assembled position.

FIG. 5 shows an enlarged front distal-side view of the hollow shaft in the direction V-V according to FIG. 2.

FIG. 8a shows an enlarged, cut-out side view of a second embodiment of detail VIII according to FIG. 1, but showing the tool in the installation position.

FIG. 8b shows a non-cut-out overhead view of the depiction according to FIG. 8a.

FIG. 9b shows a non-cut-out overhead view of the depiction according to FIG. 9a.

DETAILED DESCRIPTION OF THE INVENTION

Figure 1:
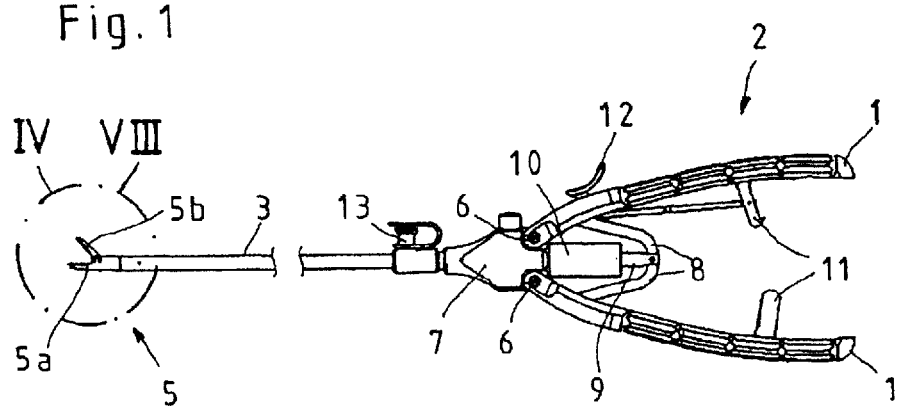
FIG. 1 shows a schematic side view of an inventive tubular shaft instrument.
Figure 2:
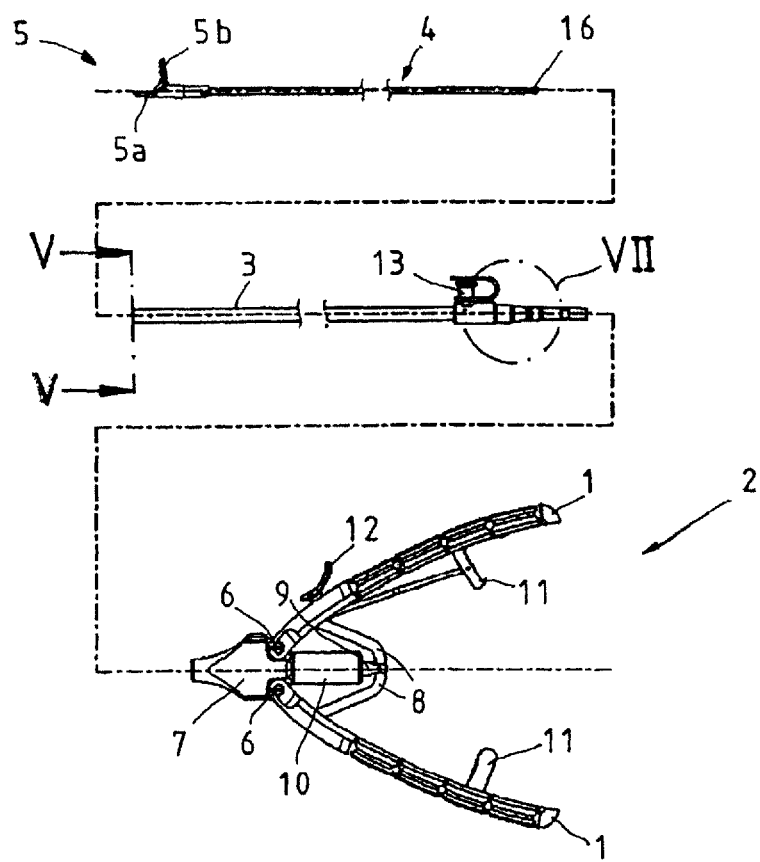
FIG. 2 shows a schematic side view of the instrument according to FIG. 1 but in disassembled form.

The tubular medical instrument shown in FIGS. 1 and 2, configured as a needle holder, consists essentially of a handle 2 equipped with two gripping members, a hollow shaft 3, and a tool actuation element 4 that can be inserted into the hollow shaft 3 and has on its distal end a tool 5 consisting of two jaw members 5a and 5b. In the illustrated embodiment the tool actuation element 4 is configured as a push-pull rod 4. Other configurations of the tool actuation element 4 are can also be used, of course, as for instance the configuration as torsion bar.

The components especially clearly shown in FIG. 2—handle 2, hollow shaft 3, and push-pull rod 4—can be coupled to one another by coupling and snap-on mechanisms in such a way that by actuating the gripping members of the handle 2, the jaw members 5a and 5b of the tool 5 can be moved between an open and a closed working position, in such a way that the forces exerted by the user on the gripping members 1 of the handle 2 are transmitted by the push-pull rod 4 onto the jaw members 5a, 5b of the tool 5.

As an alternative to the illustrated configuration of the handle 2 with two gripping members 1, it is also possible to actuate the push-pull rod 4 for instance by an actuation mechanism mounted on the handle 2 in the form of an axially movable slider element. Likewise the tool 5 can consist, for instance, of a knife that can be coupled with the push-pull rod 4 and that can be slid by the push-pull rod 4 exclusively in the axial direction.

As can be seen from FIGS. 1 and 2, in the illustrated embodiment both gripping members 1 of the handle 2 are configured as rotatable gripping members 1, which are mounted on a housing 7 of the handle 2 so that they can rotate over contact points 6. To convert the rotary motion of the gripping members 1 into a purely axial motion of the push-pull rod 4 and for power transmission of the pushing and/or pulling force exerted by the user through the handle 2 on the push-pull rod 4, both gripping members 1 are connected each by an articulated lever 8 with a coupling rod 9, which in turn is directly or indirectly coupled by a coupling mechanism with the push-pull rod 4, in such a way that the coupling of the push-pull rod 4 with the coupling rod 9 and thus with the handle 2 occurs inside the coupling housing 10.

Figure 9A:
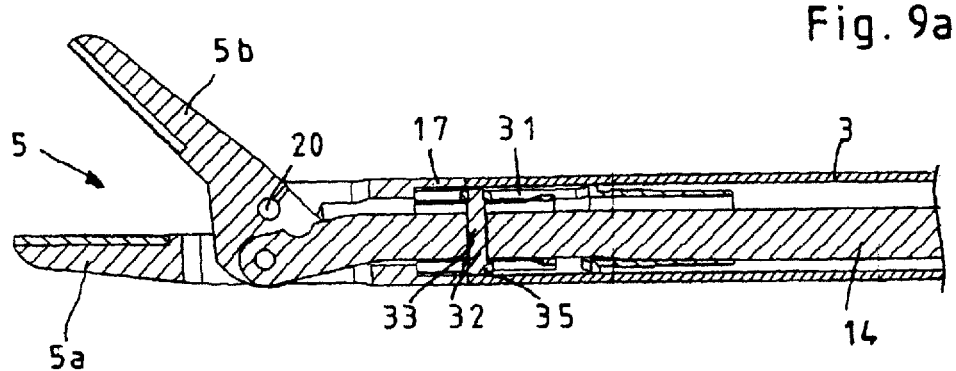
FIG. 9a shows an enlarged, cut-out side view of the second embodiment of detail VIII according to FIG. 1, showing the tool in the open working position.

The coupling of the push-pull rod 4 and thus also of the jaw members 5a and 5b of the tool 5 with the gripping members 1 of the handle 2 is arranged in such a way that upon pressing together the gripping members 1, the push-pull rod 4 is drawn in the axial direction to the proximal end of the instrument by the articulated lever and the coupling rod 9. This axial sliding of the push-pull rod 4 toward the proximal end of the instrument causes a conversion of the jaw members 5a, 5b of the tool 5 into the closed working position, as shown in FIGS. 6c and 9c. In this compressed position the gripping members 1 can be fixed with respect to one another by a stopping device 11, so that the user is not required to continuously exert pressure on the gripping members 1 of the handle 2. This fixing can be released again by means of an unlocking bolt 12, which severs the parts of the stopping device 11.

As an alternative to the illustrated embodiment, it is also possible to configure the coupling of the push-pull rod 4 and thus also of the jaw members 5a and 5b of the tool 5 with the gripping members 1 of the handle 2 in such a way an axial sliding of the push-pull rod 4 toward the distal end of the instrument causes a conversion of the jaw members 5a, 5b of the tool 5 into the closed working position.

The gripping members are advantageously pre-tensed by a spring element in the open position, such that the spring element can be positioned in the coupling housing 10. As soon as the unlocking button 12 is actuated, this spring element pushes the push-pull rod 4 in the axial direction toward the distal end of the instrument, so that the gripping members 1 are pressed apart by the coupling rod 9 and the articulated lever 8. This axial sliding of the push-pull rod 4 toward the distal end of the instrument causes a conversion of the jaw members 5a, 5b of the tool 5 into the open working position, as is shown in FIGS. 6b and 9a.

As an alternative to the illustrated embodiment of the handle 2 with two rotatable gripping members 1, it is also possible of course to configure just a single gripping member 1 so that it can rotate, whereas the other gripping member in that case can be configured as a single piece, for instance, that is rigid with the housing 7 of the handle 2. In such a configuration it is also possible to couple the push-pull rod 4 directly with the rotatable gripping member 1.

In addition it is possible, in the coupling area of the push-pull rod 4 with the handle 2, to provide an overload protector, which prevents too great an exertion of force into the push-pull rod 4. Such an overload protection can be positioned as an overload spring, for instance, in the area of the coupling rod 9.

The hollow shaft 3 that serves for the insertion of the push-pull rod 4 can be coupled with the handle 2 by means of a coupling or snap-on mechanism, which is positioned in the housing 7 of the handle 2. In the illustrated embodiment of the tubular medical instrument the hollow shaft 3 comprises in addition a rinsing connection 13, which on the one hand serves to introduce liquid during an operation and on the other hand can have a rinsing hose connected to it to cleanse the hollow shaft 3.

The structure of the push-pull rod 4 and of the coupling mechanism for detachably connecting the push-pull rod 4 with the hollow shaft 3 can be seen in particular from FIGS. 3 through 6c and FIGS. 8a through 9c.

As can be seen in particular from FIGS. 3 and 4, the push-pull rod consists of a rod base body 14 as well as a tool assembly 15 that makes up the distal end of the push-pull rod 4, so that the tool assembly 15 that bears the rotatable jaw member 5b can be firmly connected with the rod base body 14, for instance by soldering, bolting, or cementing. On the proximal end the push-pull rod 4 comprises a coupling element 16, which serves to connect the push-pull rod 4 with the handle 2.

The structure of the tool assembly 15 can be seen in particular from FIGS. 4 and 6a through 6c as well as 8a through 9c.

In the first embodiment shown in FIGS. 4 and 6a through 6c, the tool assembly 15 consists of a sleeve 17, which is configured as a single unit with a jaw member of the tool 5 that is configured as a rigid jaw member 5a. A tool shaft 18 is mounted in the sleeve 17 so that it can slide in the axial direction, and said shaft is connected on the distal side with the rotatable jaw member 5b of the tool 5 by an articulated lever 19 and on the proximal side can be connected firmly with the rod base body 14. To allow the axial sliding of the push-pull rod 4 to be transmitted directly and as free as possible of play to the rotatable jaw member 5b by the tool shaft 18, the articulated lever 19 is mounted so that it can rotate both on the rotatable jaw member 5b and on the tool shaft 18. The sleeve 7 equipped with a rigid jaw member 5a and the tool shaft 18 are connected or coupled to one another by the rotatable jaw member 5b and a rigid rotation axle 20 of the rotatable jaw member 5b, in such a way that the rotation axle 20 is mounted in the sleeve 17.

As an alternative to the illustrated embodiment, it is also possible of course to equip the tool 5 with two jaw members 5b that can rotate with respect to one another.

Finally, the structure and the functioning of the coupling mechanism of this first embodiment can be seen from FIGS. 4 through 6c, by which mechanism the push-pull rod 4 and the hollow shaft 3 can be detachably connected to one another.

This coupling mechanism is configured as a peg-and-groove control 21, which in the illustrated embodiment consists of two helical-shaped guide tracks 22 that are configured in the sleeve 17 of the tool assembly 15 and of two control pegs 23 configured on the distal inner side of the hollow shaft 3 for insertion in the guide tracks 22.

As can be seen from FIG. 5, in the illustrated embodiment two control pegs 23 are configured opposite to one another on the distal inside of the hollow shaft 3. This configuration of two control pegs 23 and two corresponding guide tracks 22, positioned opposite to one another, has the advantage that the two components that are to be coupled to one another—the hollow shaft 3 and the push-pull rod 4—can be coupled to one another not only in a single position of the two components, so that the installation is simplified.

To avoid self-locking of the control peg 23 during insertion or removal from the guide tracks 22, the guide tracks 22 should preferably be helical-shaped and should comprise a gradient angle Alpha, which should not exceed a predetermined maximum gradient, preferably, of 45 degrees, depending on the friction pairing.

As an alternative to the illustrated embodiment, it is also possible of course to configure the peg-and-groove control 21 in such a way that the at least one control peg 23 on the tool assembly 15 of the push-pull rod 4 and the guide tracks 22 for insertion of the control peg 23 are positioned on the distal end of the hollow shaft 3.

In addition, an open recess 24 running on the proximal side in the axial direction of the tool shaft 18 for locking insertion of the control peg 23, with the tubular instrument in assembled working position, is configured in the tool shaft 18. At least one of the edges 24a of the recess 24 running essentially parallel to one another in the axial direction of the tool shaft 18, with the tool 5 in the working position, form a limiting abutment surface for every control peg 23 and thus prevent independent unwinding out of the corresponding guide track 22.

Figure 7:
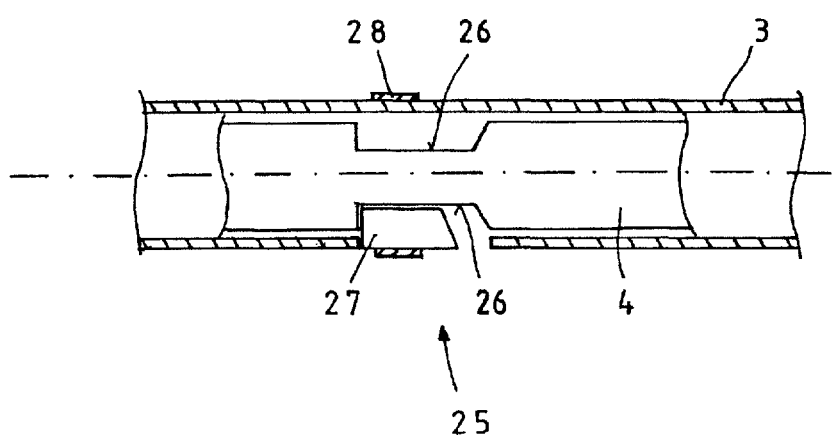
FIG. 7 shows a partly cut-out schematic overhead view of detail VII according to FIG. 2.

In addition to this previously described securing of the coupling mechanism, intended to prevent accidental conversion of the tool 5 into the extra-open installation position, the illustrated tubular instrument in the area of the proximal end of the push-pull rod 5 and of the hollow shaft 3 comprises a bayonet-type device 25, which limits the mobility of the push-pull rod 4 inside the hollow shaft 3, as shown schematically in FIG. 7.

The limiting device 25 is also designed to prevent unintentional uncoupling of the tool actuation element 4 or of the push-pull rod 4 and of the hollow shaft 3 by conversion of the tool 5 into the extra-open installation position.

As can be seen from FIG. 7, the limiting device 25 in the illustrated embodiment consists of two contact surfaces 26 configured on the tool actuation element 4 and positioned opposite to one another, which are configured as recesses in the tool actuation element 4, as well as of a contact element 27 that is mounted in a recess in the hollow shaft 3 and, with the tool actuation element 4 and the hollow shaft 3 installed, is essentially in form-locking contact on one of the contact surface 26 of the tool actuation element 4.

In the working position of the limiting device 25 illustrated in FIG. 7, which also corresponds to the position assumed by the limiting device 25, when the hollow shaft 3 with inserted tool actuation element 4 (push-pull rod 4) is coupled with the handle 2, the contact element 27, on the one hand, is in form-locking contact with one of the contact surfaces 26 and, on the other hand, is flush with the peripheral surface of the hollow shaft 3, so that the insertion of the hollow shaft 3 into the handle 2 can proceed without problem. Because the axial extension of the contact surfaces 26 exceeds the axial length of the contact element 27, it is possible to push the tool actuation element 4 (push-pull rod 4) as far as this difference in length in the axial direction inside the hollow shaft 3. This possible axial motion of the tool actuation element 4 (push-pull rod 4) corresponds exactly to the axial sliding of the tool actuation element 4 (push-pull rod 4) that is necessary in order to convert the tool 5 from the closed to the open working position and back again.

The conversion of the tool into the extra-open working position of the tool 5, which is necessary for uncoupling of the tool actuation element 4 (push-pull rod 4) and the hollow shaft 3, is prevented however by the contact element 27 because said element on the one hand forms a direct abutment for the tool actuation element 4 (push-pull rod 4) in an additional axial sliding, and on the other hand a radial motion of the contact element 27 outward is prevented by the integration into the handle 2.

In addition to the restriction of the axial motion of the tool actuation element 4 (push-pull rod 4), the limiting device 25 in the illustrated embodiment of the tool actuation element 4 as a push-pull rod 4 serves to hinder a torsion of the push-pull rod 4 around its longitudinal axis.

Figure 6A:
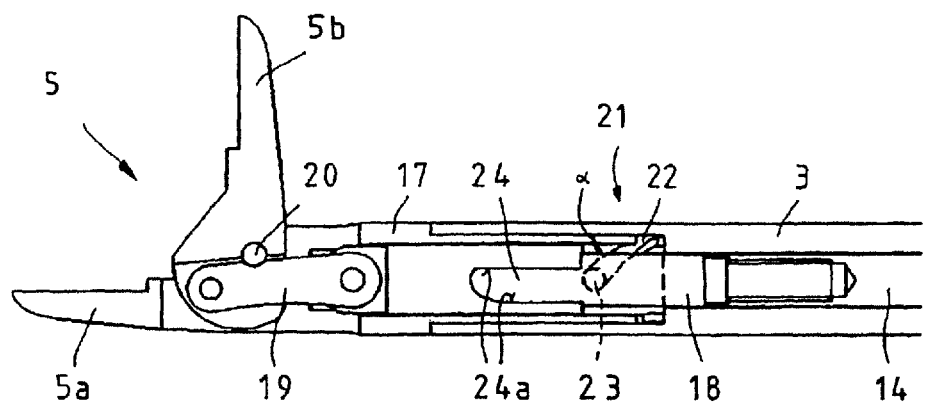
FIG. 6*a* shows an enlarged, partly cut-out side view of the first embodiment of detail IV according to FIG. 1, but showing the tool in assembled position.
Figure 6B:
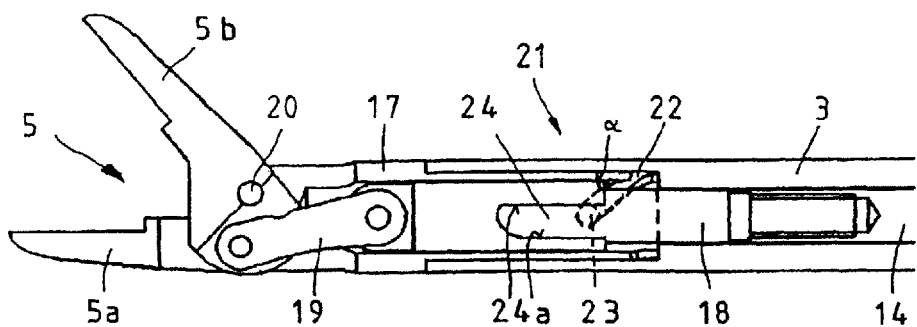
FIG. 6*b* presents a depiction according to FIG. 6*a*, with the tool seen in open working position.
Figure 6C:
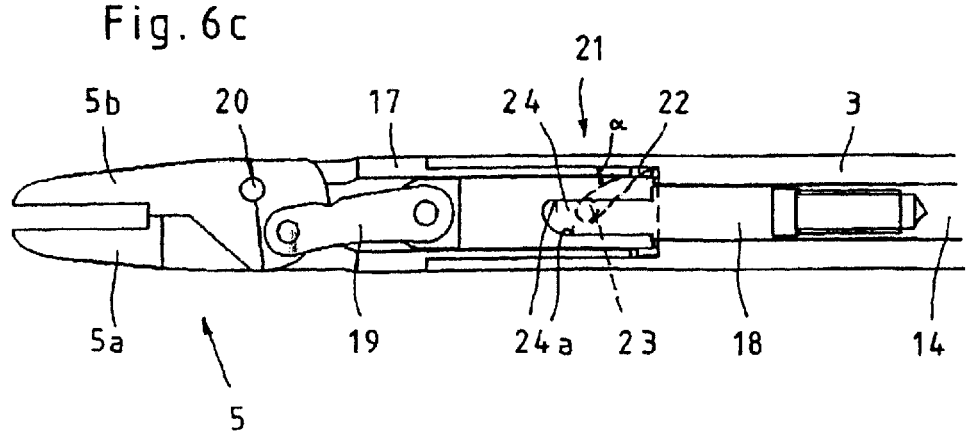
FIG. 6c presents a depiction according to FIG. 6a, but showing the tool in the closed working position.

As soon as the hollow shaft 3 with the tool actuation element 4 (push-pull rod 4) mounted in it is again uncoupled from the handle 2, it is possible, by exerting pressure on the uncoupled proximal end of the tool actuation element 4 (push-pull rod 4) to push this element in the distal direction until the tool 5 assumes the extra-open installation position illustrated in FIG. 6a. Because, when the contact element 27 is uncoupled from the handle 2, said element can be pressed outward in the axial direction, as soon as a greater pressure is exerted on the uncoupled proximal end of the tool actuation element 4 (push-pull rod 4), the limiting device 25, uncoupled from the handle 2, is disabled and thus allows the uncoupling of the hollow shaft 3 and the tool actuation element 4 (push-pull rod 4).

To facilitate the handling of the limiting device 25, the contact element 27, as seen in FIG. 7, is held in the recess configured in the hollow shaft 3 by an elastic rubber ring 28. This spring-elastic mounting of the contact element 27 allows, on the one hand, the continuation of the radially outward-directed exiting of the contact element 27 for the release of the tool actuation element 4 (push-pull rod 4) and, on the other hand, ensures the correctly positioned reinsertion of the contact element into the recess of the hollow shaft 3, so that the limiting device 25 is converted immediately back into operationally ready condition. The elastic rubber ring 28, however, serves primarily to prevent the contact element 27 from falling out of the recess in the hollow shaft 3.

The previously described operation of the limiting device 25, independently of the practical advantages of the rubber ring 28, is completely independent of the use of the rubber ring 28.

In addition to the previously described securing methods, intended to prevent accidental conversion of the tool 5 into the extra-open installation position, or alternatively in addition to at least one of these securing methods, it is possible structurally to restrict the angle of rotation of the gripping members 1 of the handle 2 with respect to one another in such a way that the gripping members, with the tubular instrument fully installed, cannot be converted into a position that causes the conversion of the tool 5 into the extra-open installation position.

In the second embodiment, shown in FIGS. 8a through 9c, the tool assembly 15 consists likewise of a sleeve 17, which is configured as a single unit with a jaw member of the tool 5 that is configured as a rigid jaw member 5a. The rod base body 14 of the push-pull rod 4 is mounted so that it can slide in the axial direction in the sleeve 17 and on the distal side it is connected with the rotatable jaw member 5b of the tool 5. To allow the axial sliding of the push-pull rod 4 to be transmitted directly onto the rotatable jaw member 5b, and as free of play as possible, the rod base body 14 is mounted rotatably on the rotatable jaw member 5b. The sleeve 17 equipped with the rigid jaw member 5a and the rod base body 14 are connected or coupled to one another by the rotatable jaw member 5b and a rigid rotation axle 20 of the rotatable jaw member 5b, in such a way that the rotation axle 20 is mounted in the sleeve 17.

Finally, FIGS. 8 through 9c according to this second embodiment indicate the structure and functioning of the coupling mechanism, by which the push-pull rod 4 and the hollow shaft 3 can be connected to one another.

This coupling mechanism is configured as a bayonet-type connection 29, which consists of at least one longitudinal cavity 30 configured in the sleeve 17 of the tool assembly 15 and of at least one control peg configured on the distal inside of the hollow shaft 3 in the manner of the control peg 23 as shown in FIG. 5 for insertion in the longitudinal cavity 30.

A sleeve-shaped guide assembly 31 is also positioned in the sleeve 17 and coaxially surrounds the distal end of the rod base body 14. In the area of its distal end, positioned in the guide assembly 31, the rod base body 14 comprises a locking pin 32 that is positioned perpendicularly to the longitudinal axis of the rod base body 14 and is mounted so that it can move freely in a bore-hole 33 of the rod base body 14 in such a way that the free ends of the locking pin 32 penetrate on both sides through the guide tracks 34 configured in the guide unit 31. The free ends of the locking pin 32 that extend beyond the guide tracks 34 are configured in the illustrated embodiment as bolt-head-shaped thickenings 35, which prevent the locking pin 32 from slipping out of the guide tracks 34 and bore-hole 33.

The assembling of the illustrated tubular instrument and in particular of the coupling mechanism for connecting the hollow shaft 3 with the push-pull rod 4 is described below with reference to FIGS. 6a through 6c and FIGS. 8a through 9c for both embodiments.

Embodiment According to FIGS. 6a Through 6

To start the assembly, the tool 5 is converted into the installation position illustrated in FIG. 6a by opening the jaw members 5a and 5b, and in said position the rotatable jaw member 5b is found in an extremely wide-opened position, into which the jaw member 5b of the assembled tubular instrument cannot be converted.

In this installation position the hollow shaft 3, with its distal end foremost, is pushed onto the push-pull rod 4 until the distal end is in contact with the sleeve 7 of the tool assembly 15. The hollow shaft 3 and push-pull rod 4 components are coupled then by rotating the components with respect to one another until the control pegs engage in the guide tracks 22. Then the components 3 and 4 are rotated further with respect to one another until the control peg 23 has reached the end of the guide track 22.

If the push-pull rod 4 is drawn in the axial direction all the way to the proximal end or else the jaw members 5a, 5b are pressed together, the control peg 23 positioned in the guide track 22 enters the recess 24 configured in the tool shaft 18.

FIGS. 6b and 6c show the tool 5 in the two extreme working positions of the jaw members, that is, the open working position according to FIG. 6b and the closed working position according to FIG. 6c. As can be seen from the appended illustrations, the control peg 23 in these positions is in contact with the upper edge 24a of the recess 24, so that the edge 24a forms a limiting abutment surface for the control peg 23 that prevents the control peg 23 from being rotated out of the guide track 22 again.

Thanks to this self-locking effect of the peg-and-groove control 21, in the following next assembly of the tubular instrument there is no danger that the components assembled in the first installation step—the hollow shaft 3 and the push-pull rod 4—are released again.

In the next installation steps the hollow shaft 3 and the handle 2 are snapped onto one another and the push-pull rod 4 is connected with the gripping members 1 of the handle 2.

Disassembly then occurs in exactly reverse order of the installation steps from the release of the snap-on connection between the hollow shaft 3 and the handle 2, release of the connection of the push-pull rod 4 with the gripping members 1 of the handle 2 up to the uncoupling of the hollow shaft 3 from the push-pull rod 4 by release of the peg-and-groove control 21. This requires first of all that the tool 5 be converted into the installation position by a light blow or exertion of pressure by hand on the uncoupled proximal end of the push-pull rod 4 in order to release the blocking of the control peg 23 by the edge 24a of the recess 24. Then the control peg 23 can be simply rotated out of the guide track 22 to allow the hollow shaft 3 thereafter to be withdrawn from the push-pull rod 4.

Embodiment According to FIGS. 8a Through 9c

At the beginning of the installation the tool 5 is converted by opening the jaw members 5a and 5b into the installation position illustrated in FIG. 8a in which the rotatable jaw member 5b is found in an extremely wide-opened position, into which the jaw member 5b of the assembled tubular instrument cannot be converted.

In this installation position the push-pull rod 4 is pushed as far as possible in the distal direction until the locking pin 32 positioned perpendicularly to the longitudinal axis of the rod base body 14 enters a receiving element 36 configured on the inside of the sleeve 17, as shown in FIG. 8a. In this extra-open installation position of the rotatable jaw member 5b, the hollow shaft and the push-pull rod 4 can be connected to one another by the bayonet-type connection 29.

Figure 9B:
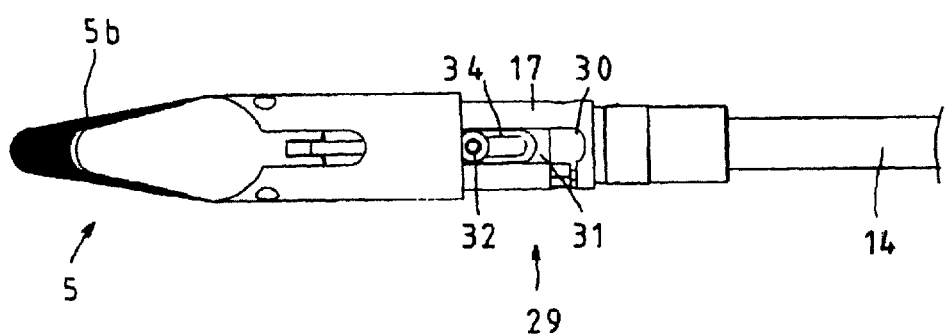
Figure 9C:
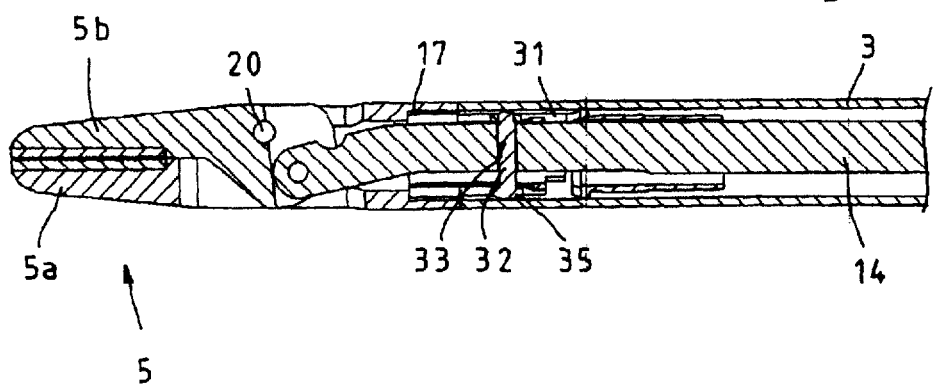
FIG. 9c shows a depiction according to FIG. 9a, but showing the tool in the closed working position.

FIGS. 9a, 9b, and 9c show the tool 5 in the two extreme working positions of the jaw members, that is, the open working position according to FIGS. 9a and 9b and the closed working position according to FIG. 9c. As can be seen from the appended illustrations, the locking pin 32 extends in these positions into the elongated cavity 30 of the bayonet-type connection 29 and thus ensures the push-pull rod 4 and thus the jaw members 5a and 5b also against rotation, so that the bayonet-type connection 29 cannot be severed in the working positions.

The up and down pendulum motion of the push-pull rod 4 that can be viewed from the illustrations in FIGS. 9a and 9c on displacing the jaw members 5a and 5b between the closed working position (FIG. 9c) and the open working position (FIGS. 9a and 9b) has no impact on the locking intervention of the locking pins 32 into the longitudinal cavity 30 because the locking pin 32 is mounted so that it will be freely movable in the bore-hole 33 of the rod base body 14.

In the next installation steps the hollow shaft 3 and the handle 2 are snapped together, and the push-pull rod 4 is connected with the gripping members 1 of the handle 2.

Disassembly then follows in the exact reverse order of the installation steps by release of the snap-on connection between the hollow shaft 3 and the handle 3, the release of the connection of the push-pull rod 4 with the gripping members 1 of the handle 2 all the way to the uncoupling of the hollow shaft 3 from the push-pull rod 4 by releasing the bayonet connection 29.

What is claimed is:

1. A tubular medical instrument having a hollow shaft, a handle positioned on the proximal end of the shaft, and at least one tool actuation element that is positioned in the hollow shaft and has on its distal end a tool consisting of two jaw members, and wherein the tool actuation element is coupleable with at least one actuation mechanism of the handle to actuate the tool between a closed working position and an open working position and wherein the tool actuation element and the hollow shaft are detachably connectable to one another by a coupling mechanism characterized in that a stopping of the coupling mechanism between the tool actuation element and the hollow shaft is dependent on the mutual opening position of the jaw members of the tool relative to each other in such a way that the tool actuation element can only be connected by the coupling mechanism with the hollow shaft exclusively in a wide-opened installation position of the jaw members of the tool that differs from the working positions of the jaw members of the tool and wherein the coupling mechanism prevents the tool from transitioning between the working positions and the installation position while the tool actuation element is coupled to the handle.

2. The tubular medical instrument according to claim 1, characterized in that the coupling mechanism is configured in the manner of a bayonet-type connection.

3. The tubular medical instrument according to claim 1, characterized in that the coupling mechanism is configured as a self-locking peg-and-groove control.

4. The tubular medical instrument according to claim 3, characterized in that the peg-and-groove control consists of at least one control peg configured on one of the components to be coupled to one another and of at least one guide track configured on the respective other component for reception of a control peg, and that at least one control peg inserted into a guide track is blocked with the tool in the working position to prevent removal from the guide track.

5. The tubular medical instrument according to claim 4, characterized in that the at least one control peg is configured on the distal-end inside of the hollow shaft.

6. The tubular medical instrument according to claim 5, characterized in that a control peg is configured on the inside of the distal end of the hollow shaft and two guide tracks for insertion of the at least one control peg are configured opposite to one another on the distal end of the tool actuation element.

7. The tubular medical instrument according to claim 4, characterized in that the guide track is configured in a helical shape and comprises a gradient angle Alpha, which does not exceed a pre-determined maximum gradient of about 45 degrees.

8. The tubular medical instrument according to claim 1, characterized in that the actuation mechanism of the handle is configured as a gripping member positioned to rotate on the handle.

9. The tubular medical instrument according to claim 1, characterized in that at least one jaw member of the tool can rotate with respect to the other jaw member by the tool actuation element.

10. The tubular medical instrument according to claim 1, characterized in that the tool actuation element is configured as a push-pull rod.

11. The tubular medical instrument according to claim 10, characterized in that the push-pull rod consists of a rod base body and a tool assembly that can be combined with the rod base body and forms the distal end of the push-pull rod.

12. The tubular medical instrument according to claim 11, characterized in that the tool assembly consists of a sleeve equipped with a rigid jaw member of the tool and a tool tube mounted so that it can slide in the sleeve, and said shaft on the one hand is coupled with a rotatable jaw member of the tool and on the other hand can be combined firmly with the rod base body.

13. The tubular medical instrument according to claim 12, wherein the coupling mechanism is configured as a self-locking peg-and-groove control, and the peg-and-groove control consists of at least one control peg configured on one of the components to be coupled to one another and of at least one guide track configured on the respective other component for reception of a control peg, and that at least one control peg inserted into a guide track is blocked with the tool in the working position to prevent removal from the guide track, and a recess open on the proximal side and running in the axial direction of the tool shaft is configured in the tool shaft of the tool assembly for insertion of the control peg.

14. The tubular medical instrument according to claim 13, characterized in that at least one of the edges of the recess that run essentially parallel to one another in the axial direction of the tool shaft forms a limiting abutment surface for the control peg when the tool is in the working position.

15. The tubular medical instrument according to claim 12, characterized in that a guide track for insertion of a control peg is configured in the sleeve of the tool assembly.

16. The tubular medical instrument according to claim 12, characterized in that the tool assembly and the rotatable jaw member are connected to one another by at least one articulated lever mounted so that the at least one articulated lever can rotate on both sides.

17. The tubular medical instrument according to claim 1, characterized in that in the area of the proximal end of the tool actuation element that is mounted in the handle, and of the hollow shaft, a limiting device is positioned that limits the mobility of the tool actuation element inside the hollow shaft.

18. The tubular medical instrument according to claim 17, characterized in that the limiting device consists of at least one contact surface configured on the tool actuation element and a contact element that can be brought into active connection with this contact surface and is mounted in the hollow shaft.

19. The tubular medical instrument according to claim 17, characterized in that two contact surfaces configured as recesses opposite to one another are positioned on the tool actuation element, and a contact element is mounted in a recess in the hollow shaft and, when the tool actuation element and the hollow shaft are assembled, is in essentially form-locking contact with one of the contact surfaces of the tool actuation element.

20. The tubular medical instrument according to claim 1, characterized in that the tool can be converted into the installation position by a blow on the proximal end of the tool actuation element for uncoupling the tool actuation element from the hollow shaft.

21. The tubular medical instrument according to claim 1, characterized in that the tool actuation element configured as a push-pull rod consists of a rod base body and a tool assembly that can be firmly connected with the rod base body and forms the distal end of the push-pull rod, wherein the tool assembly consists of a sleeve equipped with a rigid jaw member of the tool and a guide assembly that is positioned in the sleeve and coaxially surrounds the distal end of the push-pull rod.

22. The tubular medical instrument according to claim 21, characterized in that the push-pull rod, in the area of its distal end mounted in the guide assembly, comprises a locking pin positioned perpendicularly to the longitudinal axis of the push-pull rod.

23. The tubular medical instrument according to claim 2, characterized in that the locking pin is mounted so that it can move freely in a bore-hole of the push-pull rod in such a way that the free ends of the locking pin penetrate in the guide tracks configured in the guide assembly.

24. The tubular medical instrument according to claim 2, characterized in that the free ends of the locking pin are configured as bolt-head-shaped thickenings.

* * * * *